(12) United States Patent
Wax et al.

(10) Patent No.: US 11,460,292 B2
(45) Date of Patent: Oct. 4, 2022

(54) OPTICAL COHERENCE TOMOGRAPHY DEVICE AND SYSTEM

(71) Applicant: Duke University, Durham, NC (US)

(72) Inventors: Adam Wax, Durham, NC (US); Michael Crose, Durham, NC (US); William Brown, Durham, NC (US)

(73) Assignee: Duke University, Durham, NC (US)

( * ) Notice: Subject to any disclaimer, the term of this patent is extended or adjusted under 35 U.S.C. 154(b) by 677 days.

(21) Appl. No.: 16/478,300

(22) PCT Filed: Jan. 17, 2018

(86) PCT No.: PCT/US2018/014057
§ 371 (c)(1),
(2) Date: Jul. 16, 2019

(87) PCT Pub. No.: WO2018/136518
PCT Pub. Date: Jul. 26, 2018

(65) Prior Publication Data
US 2019/0368861 A1    Dec. 5, 2019

Related U.S. Application Data

(60) Provisional application No. 62/446,949, filed on Jan. 17, 2017.

(51) Int. Cl.
*G01B 9/02091* (2022.01)
*A61B 3/12* (2006.01)
(Continued)

(52) U.S. Cl.
CPC .......... *G01B 9/02091* (2013.01); *A61B 3/12* (2013.01); *A61B 5/0035* (2013.01);
(Continued)

(58) Field of Classification Search
CPC ............ G01B 9/02091; G01B 9/02054; G01B 9/02044; A61B 3/12; A61B 5/0035; A61B 5/0066; A61B 3/102; G01J 3/45
See application file for complete search history.

(56) References Cited

U.S. PATENT DOCUMENTS 6,293,674 B1 *  9/2001 Huang ...................... G06T 7/60
                                                            351/221
9,055,903 B2 *  6/2015 Higuchi ............. G01B 9/02068
(Continued)

FOREIGN PATENT DOCUMENTS

CN       101677767 A     3/2010
CN       202699100 U     1/2013
(Continued)

OTHER PUBLICATIONS

Extended European Search Report issued in EP Patent Application No. 18741766.2 dated Sep. 9, 2020.
(Continued)

*Primary Examiner* — Jonathan M Hansen
(74) *Attorney, Agent, or Firm* — Kaplan Breyer Schwarz, LLP (57) ABSTRACT

An optical coherence tomography (OCT) scan device includes an OCT scan device housing, an interferometer disposed in within the OCT scan device housing and including a light source, a fiber optic coupler including an interferometer output, a reference-arm, and a sample-arm. The OCT scan device further includes a power source configured to provide power to the light source and the remaining components of the OCT scan device, and a controller disposed within the OCT scan device housing and configured to adjust lens focusing parameters in the reference-arm and the sample-arm, and control a scanning function of an optical beam emitting from the sample-arm. The OCT scan
(Continued)

device is further configured to transmit and receive control instructions and transmit fundus image data.

12 Claims, 5 Drawing Sheets (51) Int. Cl.
A61B 5/00 (2006.01)
G01J 3/02 (2006.01)
G01J 3/45 (2006.01)

(52) U.S. Cl.
CPC .......... *A61B 5/0066* (2013.01); *G01J 3/0208* (2013.01); *G01J 3/45* (2013.01)

(56) References Cited

U.S. PATENT DOCUMENTS

| | | | |
|---|---|---|---|
| 2010/0033676 A1 | 2/2010 | De Vries et al. | |
| 2012/0293807 A1* | 11/2012 | Sugita | A61B 3/102 356/479 |
| 2012/0310081 A1 | 12/2012 | Adler et al. | |
| 2013/0194581 A1 | 8/2013 | Hirofumi | |
| 2014/0028997 A1 | 1/2014 | Cable et al. | |
| 2015/0055137 A1* | 2/2015 | Brown | G01B 9/02054 356/479 |
| 2015/0173606 A1 | 6/2015 | Yu et al. | |
| 2015/0327761 A1 | 11/2015 | Narasimha-Iyer et al. | |
| 2016/0100754 A1 | 4/2016 | Dobashi | |
| 2018/0153401 A1* | 6/2018 | Strózyk | A61B 3/12 |

FOREIGN PATENT DOCUMENTS

| | | |
|---|---|---|
| CN | 103222852 A | 7/2013 |
| CN | 104755908 A | 7/2015 |
| CN | 105848561 A | 8/2016 |
| WO | 2015/052071 A1 | 4/2015 |
| WO | 2015/189174 A2 | 12/2015 |
| WO | 2016/068707 A2 | 5/2016 |

OTHER PUBLICATIONS

Office Action issued in Chinese patent application No. 201880012329. 6, dated May 25, 2021, 24 pp. w/ translation.
Office Action issued in Chinese patent application No. 201880012329. 6, dated Nov. 30, 2021, 18 pp. w/ translation.
Authorized Officer: Lee W. Young, International Search Report and Written Opinion issued in PCT application No. PCT/US 18/14057, dated May 8, 2018, 12 pp.
Yogesh Rao et al., "Modeling and Simulation of Optical Coherence Tomography on Virtual OCT", "Procedia Computer Science", Dec. 1, 2018, pp. 640-650, 15 (2015), https://ac.els.cdn.com/S1877050915003579/1-s2.0-S1877050915003579-main.pdf?_tid=3096f192-1640-4c8a-93de-b4e172e7ed8f&acdnat=1524678732_7a0d25d64decb64aa689e2407479451f.
Office Action issued in Chinese patent application No. 201880012329. 6, dated Apr. 20, 2022, 23 pp. w/ translation.

* cited by examiner

FIG. 5

# OPTICAL COHERENCE TOMOGRAPHY DEVICE AND SYSTEM

BACKGROUND

Optical coherence tomography (OCT) is one of a class of optical tomographic techniques. A relatively recent implementation of optical coherence tomography—frequency-domain optical coherence tomography—provides advantages in signal-to-noise ratio, permitting faster signal acquisition. Commercially available OCT systems are employed in diverse applications, including art conservation and diagnostic medicine, notably in ophthalmology and optometry where it can be used to obtain detailed images from within the retina.

OCT is based on low-coherence interferometry, typically employing near-infrared light or white light interferometry (WLI) corresponding to each wavelength. The use of relatively long wavelength light allows it to penetrate the scattering medium. Depending on the properties of the light source, optical coherence tomography has achieved submicrometer resolution.

OCT typically uses low coherence light to capture micrometer-resolution, two- and three-dimensional images from within optical scattering media (e.g., biological tissue, etc.). Interferometric techniques are utilized for measuring physical quantities that can induce an optical path difference (OPD) in the interferometers. By employing a short coherence length light illuminated from wide-band light sources, such as super luminescent diode (SLD) LEDs, fringes of the interferogram are narrowly located in the zero path length difference region. Thus, the phase difference can be determined by measuring the fringe peak or the envelope peak of the interferogram.

In WLI, white light corresponding to each wavelength of a separate fringe system is produced. The electric field at any point of observation is the sum of electric fields of these individual patterns. In WLI, the interferometer is adjusted such that the optical path difference is zero at the center of the field of view, where the electric field of different wavelengths exhibits the maximum at the center point. The fringes of different wavelengths will no longer coincide when moving away from the center of the pattern. The fringe pattern is a sequence of colors whose saturation decreases rapidly. The central bright white light fringe can be used to adjust the WLI.

Light sources such as fluorescent lamp, SLDs, LEDs, Laser diodes near threshold, optically pumped Erbium-doped fibers and tungsten lamps, can be used in the WLI. In the WLI, one of the two arms is used as the measurement arm and the other one as the reference-arm. The length of the reference-arm can be typically controlled by different methods such as moving mirrors or Piezoelectric (PZT) devices. Generally, the operation of WLI is based on balancing the two arms of the interferometer and compensating the OPD in the measurement arm. Therefore, the desired measurement can be achieved.

OCT imaging systems are typically divided into several subsystems including an optical engine, a processing unit, and a scanning system. The scanning system may provide the interface to the sample that is being imaged. However, there has long been needed an OCT scan device that is portable and incorporates the optical engine and the scanning system in a single unit, separate and apart from the processing unit.

SUMMARY

It should be appreciated that this Summary is provided to introduce a selection of concepts in a simplified form that are further described below in the Detailed Description. This Summary is not intended to be used to limit the scope of the claimed subject matter.

In one embodiment disclosed herein, an optical coherence tomography (OCT) scan device including an OCT scan device housing, an interferometer disposed within the OCT scan device housing and including a light source, a fiber optic coupler including an interferometer output, a reference-arm, and a sample-arm. The OCT scan device further including a power source configured to provide power to the light source and the remaining components of the OCT scan device, and a controller disposed within the OCT scan device housing and configured to adjust lens focusing parameters in the reference-arm and the sample-arm, and control a scanning function of an optical beam emitting from the sample-arm, wherein the OCT scan device being configured to transmit and receive control instructions and transmit fundus image data.

In further embodiments, the fiber optic coupler comprises a fused fiber optic coupler.

In further embodiments, the reference-arm further includes a reference-arm collimation lens, a reference-arm lens, and a reference-arm mirror, where the reference-arm lens is at least one of controlled by a focus controller to adjust a course and fine focus of the reference-arm lens, or the controller to electronically control the reference-arm lens, where the reference-arm lens is tunable.

In further embodiments, the sample-arm further includes a sample-arm collimation lens, a sample-arm lens that is tunable, a sample-arm fold mirror, and a moveable mirror.

In further embodiments, the OCT scan device includes a fundus imaging system disposed within the OCT scan device housing, the fundus imaging system including an annular light source, a beam splitter, a fundus imaging system lens that is tunable, and a fundus CMOS imaging sensor, where the fundus imaging system senses optical energy emitted from the annular light source being reflected off a target sample and sensed at the fundus CMOS imaging sensor, and generates fundus images from the sensed optical energy.

In further embodiments, the optical beam emitting from the sample-arm being reflected off the moveable mirror passes through a central region of the annual light source and reflects off a reflective surface of the beam splitter.

In further embodiments, a beam emitted from the annual light source and reflected off a reflective surface of the beam splitter travels along a substantially similar path toward a target sample as a path of the optical beam reflected off the reflective surface of the beam splitter.

In another embodiment disclosed herein, an optical coherence tomography (OCT) system includes an OCT scan device that has an OCT scan device housing, an interferometer disposed within the OCT scan device housing, the interferometer including a light source, a beam splitter including an interferometer output, a reference-arm, and a sample-arm. The OCT scan device further includes an OCT scan device power source configured to provide power to the light source and the remaining components of the OCT scan device, and a controller disposed within the OCT scan device housing and configured to adjust lens focusing parameters in the reference-arm and the sample-arm, and to control a scanning function of an optical beam emitting from the sample-arm, where the OCT scan device is configured to transmit and receive control instructions and transmit fundus image data.

The OCT system further includes an OCT portable base including a spectrometer including a fiber input in direct communication with the interferometer output of the OCT scan device, a processor, and an OCT portable base power supply configured to provide power to the spectrometer and the remaining components of the OCT portable base, where the OCT portable base communicates with the OCT scan device.

The OCT system further contemplates wherein the spectrometer further includes an off-axis parabolic mirror, a diffraction grating for receiving and dispersing the optical beam emitted from the interferometer output, and a tall-pixel CMOS line scan sensor for sensing the dispersed optical beam.

The OCT system further contemplates wherein the OCT scan device further includes a fundus imaging system disposed within the OCT scan device housing, the fundus imaging system including an annular light source, a beam splitter, a fundus imaging system lens that is tunable, and a fundus CMOS imaging sensor, where the fundus imaging system senses optical energy emitted from the annular light source being reflected off a target sample and sensed at the fundus CMOS imaging sensor, and generates fundus images from the sensed optical energy.

The OCT system further contemplates wherein the sample-arm further comprises a movable mirror, and wherein the optical beam emitting from the sample-arm being reflected off the moveable mirror passes through the annular light source and reflects off a reflective surface of the beam splitter.

The OCT system further contemplates the sensed optical energy emitted from the annular light source and reflected off a reflective surface of the beam splitter travels along a substantially similar path toward a target sample as a path of the optical beam reflected off the reflective surface of the beam splitter.

The OCT system further contemplates the reference-arm further including a reference-arm collimation lens, a reference-arm lens, and a reference-arm mirror, where the reference-arm lens is at least one of operative to adjusting at least one of a course and fine focus of the reference-arm lens, or operative to be electronically control the reference-arm lens, where the reference-arm lens is tunable.

The OCT system further contemplates the sample-arm further including a sample-arm collimation lens, a sample-arm lens that is tunable, a sample-arm fold mirror, and a moveable mirror.

In another embodiment disclosed herein, an optical coherence tomography (OCT) system including an OCT scan device having an OCT scan device housing, interferometer disposed within the OCT scan device housing, the interferometer including a light source, a fiber optic coupler including an interferometer output, a reference-arm, and a sample-arm. The OCT scan device further including an OCT scan device power source configured to provide power to the light source and the remaining components of the OCT scan device, and a controller disposed within the OCT scan device housing and configured to adjust lens focusing parameters in the reference-arm and the sample-arm, and to control a scanning function of an optical beam emitting from the sample-arm, where an OCT scan device being configured to transmit and receive control instructions and transmit fundus image data.

The OCT system further including an OCT portable base having a spectrometer including a fiber input in direct communication with the interferometer output of the OCT scan device, a processor, an OCT portable base power supply configured to provide power to the spectrometer and the remaining components of the OCT portable base.

The OCT system further including a user interface (UI) device including a display device configured to display the fundus images and receive user interaction data regarding portions of the displayed fundus images; and a UI interface transmitter configured to receive fundus images from the OCT scan device and transmit the user interaction data relative to the displayed fundus images, where the OCT portable base transmitter communicates between the OCT scan device.

The OCT system further contemplating wherein the OCT scan device further comprises a fundus imaging system disposed within the OCT scan device housing configured to transmit the fundus image data to the UI device.

The OCT system further contemplating wherein the UI device being configured to receive user input on the touch screen display relative to the transmitted fundus image data, generate a user input control instruction based on the received user input, and transmit the user input generated control instruction to the OCT scan device configured to control a moveable mirror in the sample-arm of the OCT scan device.

The OCT system further contemplating wherein the OCT scan device transmits interferometer output data responsive to the user input generated control instruction via the interferometer output to the OCT portable base configured to process the interferometer output data at the spectrometer and generate optical coherence tomogram image data The OCT system further contemplating wherein the OCT portable base transmits the interferometer image data to the UI device

BRIEF DESCRIPTION OF THE DRAWINGS

The embodiments of the invention will be better understood from the following detailed description with reference to the drawings, which are not necessarily drawing to scale and in which.

DETAILED DESCRIPTION

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

It will be understood that although the terms first and second are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Some embodiments of the present invention will now be discussed with respect to FIGS. 1 through 5. As illustrated therein, some embodiments of the present invention include novel scanning devices for OCT imaging systems.

Conventional implementations of OCT imaging systems typically have a fixed sample interface, where the sample is aligned with the location of the light coming from the OCT system in order to obtain an OCT image. For many samples, this configuration of the OCT imaging system works, but there is a whole class of samples where it may be very difficult, or even impossible, to align the sample with respect to the OCT imaging systems. Thus, according to some embodiments of the present invention, the designs having a portable OCT scan device containing the entire optical engine may allow the sample interface portion of the OCT imaging system to be moved around to align it with the sample instead of aligning the sample to the system.

Portable probes according to some embodiments of the present invention may be lightweight so that it can be held, moved and controlled by the user. The OCT system may be relatively compact and, therefore, can be moved from location to location. Current OCT systems are typically fixed in a particular location and the samples or patients must be brought to that location. A portable OCT system according to some embodiments of the present invention can be taken to the samples or patients. This may be particularly useful for, for example, bedridden patients and for animal applications where moving the animals may be difficult on the animals or may increase the chance of infection or contamination.

The current invention seeks to improve the utility of handheld OCT systems by increasing their portability, reducing their form factor and reducing their cost. These improvements would enable wider application in areas where the large size and cost of current OCT instruments prevent their use.

Figure 1:
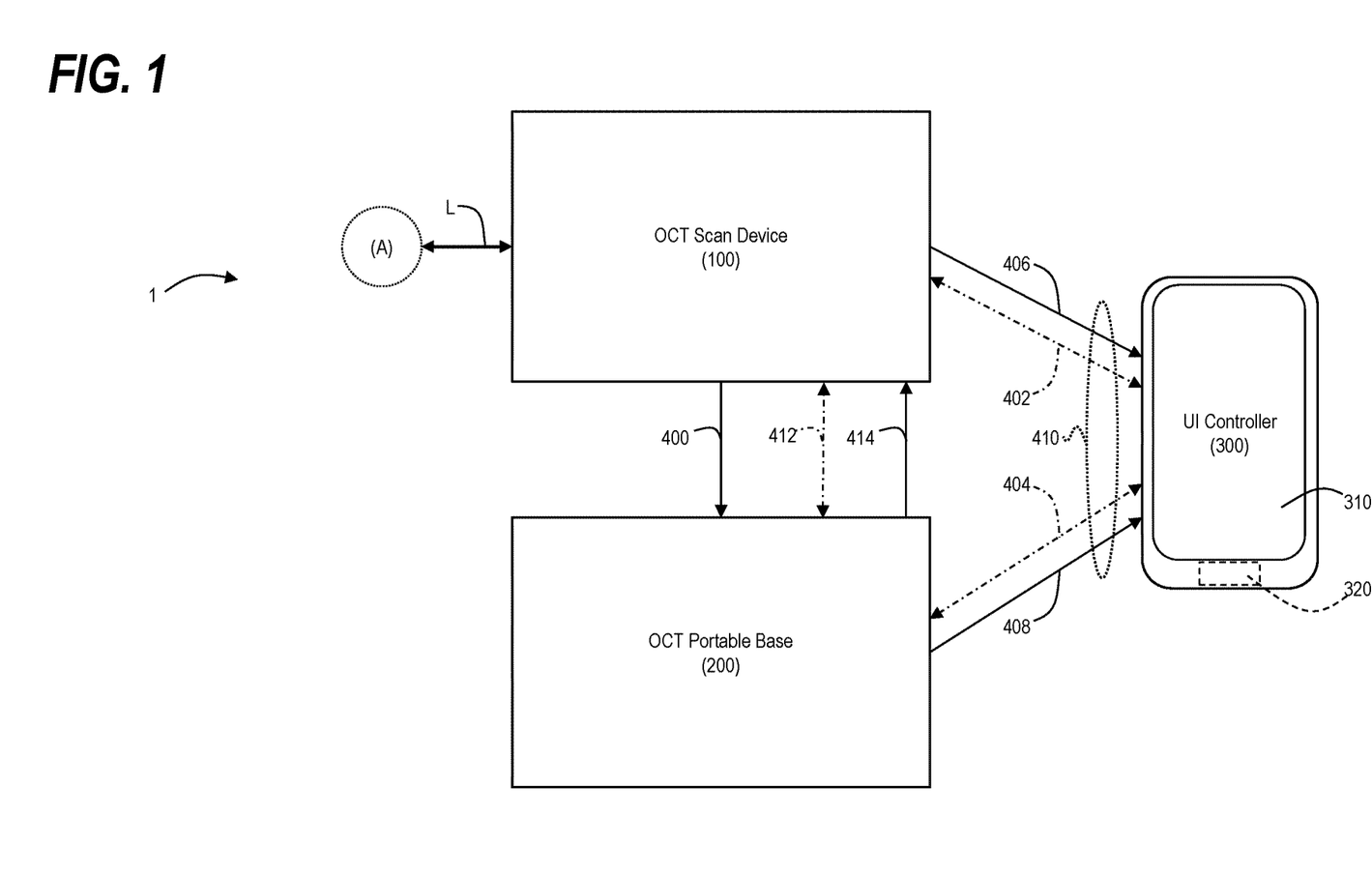
FIG. 1 illustrates a schematic diagram of the OCT system representing control signal and data signal paths between respective components.

Various embodiments of the present invention will now be discussed with respect to FIGS. 1 through 5. FIG. 1 illustrates a schematic diagram of the OCT system (1) depicting control signal and data signal paths between respective components. The OCT system (1) primarily includes three components: an OCT scan device (100), (further illustrated in more detail in FIGS. 2 and 3), an OCT portable base (200), (further illustrated in more detail in FIG. 4), and a user input (UI) controller (300). Each of these components will be discussed generally with respect to FIG. 1, and in more detail in the following figures.

The OCT scan device (100) uses low coherence light (L) to capture micrometer-resolution image data from within an optical scattering target (A). This captured data is a result of the OCT scan device (100) generating fundus image data (406) that is communicated to the UI controller (300) where a user interacts with the fundus image data (406) displayed on a touch input display device (310) to thereby generate and send OCT scan device control signals (402) back to the OCT device (100). These OCT scan device control signals (402) instruct the OCT scan device (100) to scan particular sections of the optical scattering target to thereby generate an interferometer optical output signal (400).

The OCT scan device (100) then outputs the interferometer optical output signal (400) to the OCT portable base (200) where a spectrometer, (later described), generates optical coherence tomographic data (408). The optical coherence tomographic data (408) may then be communicated to the UI controller (300) to display tomogram images on the touch input display screen (310).

Both OCT scan device control signals (402) and OCT portable base control signals (404) may be communicated to and from the UI controller (300) via UI controller wireless transceiver (320). These UI controls signals (402 and 404) in addition to the fundus image data (406) and optical coherence tomographic data (408) may be communicated to each respective device via a Bluetooth® wireless protocol (410) or an equivalent short range wireless communication protocol. In an alternative embodiment, the UI controls signals (402 and 404) in addition to the fundus image data (406) and optical coherence tomographic data (408) may be communicated to each respective device via a hardwired connection, or a combination of hardwired and wireless communication.

Additionally, optical engine control signals (412) control a tunable lens for example, a liquid tunable lens that is controlled by the tunable lens drive (178) via tunable lens control signals (180), similar to reference-arm tunable lens (134) and sample-arm tunable lens (144). The liquid tunable lenses identified below as the reference-arm lens (134), sample-arm lens (144) and the fundus imaging system lens (156) may include, for example, of a focus variable lens that uses a liquid polymer lens, the shape of which is controlled by the application of an applied voltage to quickly change or tune the particular focal length to a desired value without physical movement of the lens along its focal length axis.

In a further embodiment, the OCT portable base (200) may provide an OCT portable base power supply (414) to the OCT scan device (100). In the alternative, as later discussed below, the OCT scan device (100) may have a portable and independent power supply (190) as illustrated in FIGS. 2 and 3.

Figure 2:
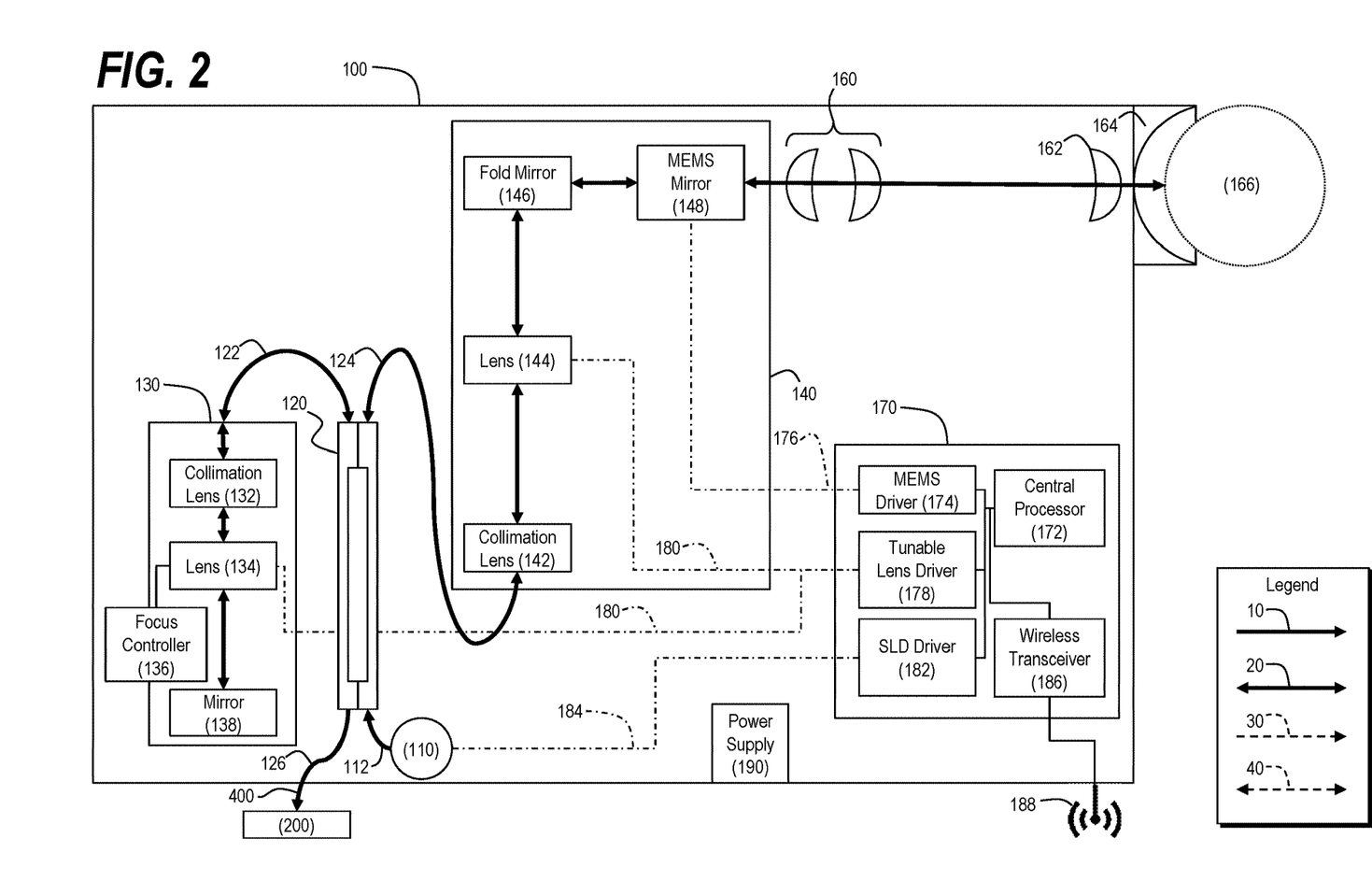
FIG. 2 illustrates a schematic diagram of a first representative embodiment of an OCT scan device.
Figure 3:
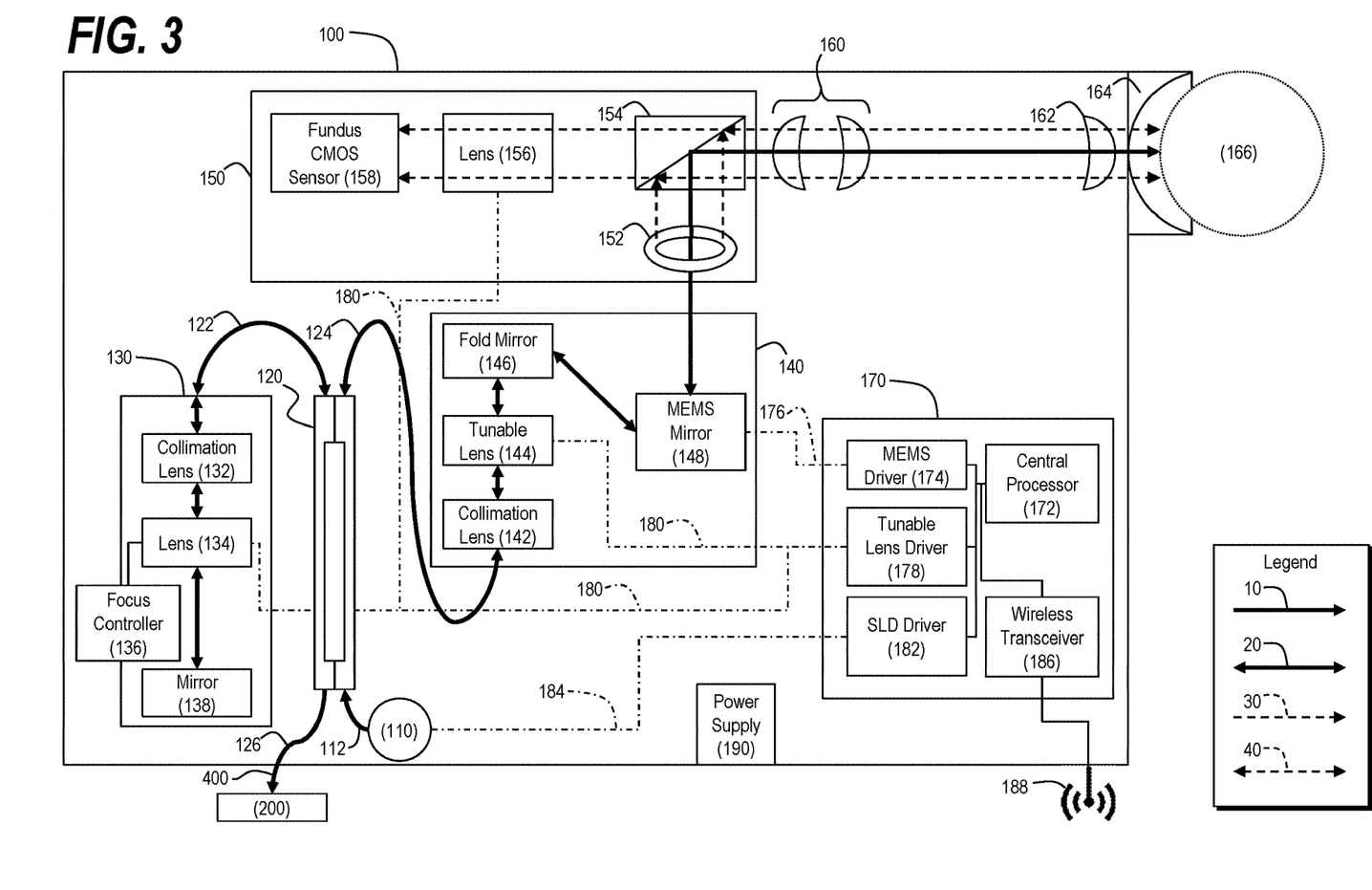
FIG. 3 illustrates a schematic diagram of a second representative embodiment of the OCT scan device illustrated in FIG. 2 including a fundus imaging system.

FIG. 2 illustrates a schematic diagram of a first representative embodiment of an OCT scan device (100). The OCT scan device (100) generally consists of an optical engine including a light source (110), (for example, a super luminescent diode (SLD), or equivalent broadband light source), an interferometer (120), a reference-arm (130), and a sample-arm (140), where the optical engine components are in communication with an OCT scan device controller (170). Each of these components will be discussed in detail below.

Note all bolded lines having a single arrow denote an optical engine uni-directional optical path (10), whereas all bolded lines having arrows on disparate ends denote an optical engine bi-directional optical path (20), (see Legend in FIG. 2).

An optical engine of the OCT scan device (100) includes the light source (110) controlled by SLD driver control signal (184) emanating from an SLD driver (182) in the OCT scan device controller (170). The light source (110) is connected to an SLD output fiber (112) that may feed into one branch of a Michelson-type optical fiber 2×2 interferometer (120). The interferometer (120) may comprise a 50:50 fiber optic coupler, or may comprise an equivalent functioning 50:50 free space beam splitter. The interferometer (120) further includes an interferometer reference-arm assembly input fiber (122) in communication with a reference-arm (130), an interferometer sample-arm assembly input fiber (124) in communication with a sample-arm (140), and an interferometer output fiber (126) outputting the interferometer optical output signal (400) of FIG. 1 to the OCT portable base (200).

The reference-arm (130) receives light from the light source (110) via the interferometer reference-arm assembly input fiber (122) which passes through a reference-arm collimation lens (132), a reference-arm lens (134), reflects off a reference-arm mirror (138) to pass back through the reference-arm lens (134), collimation lens (132) and back into the interferometer (120) via the interferometer reference-arm assembly input fiber (122). A focus controller (136) may control the reference-arm lens (134) to be focused manually in one or two focusing stages, (e.g., course and fine focusing modes), or the reference-arm lens (134) may comprise an electronically tunable lens (134), for example, a liquid tunable lens, controlled via a tunable lens control signal (180) emanating from a tunable lens driver (178) in the OCT scan device controller (170).

The sample-arm (140) receives light from the light source (110) via the interferometer sample-arm assembly input fiber (124) which passes through a sample-arm collimation lens (142), a sample-arm lens (144), reflects off a fold mirror (146) and is directed to a moveable mirror (148), (for example, a microelectromechanical system (MEMS) mirror), that may provide two-axis (X-Y) scanning of the optical light source through a focusing lens group (160) and a distal ocular lens (162), through an eye cup (164) on onto a target sample (166), (e.g., an eye, or retinal portion thereof). Reflected light from the target sample (166) travels back through the eye cup (164), the ocular lens (162), the focusing group (160), the moveable mirror (148), the fold mirror (146), lens (144) and collimation lens (142) back into the interferometer (120) via the interferometer sample-arm assembly input fiber (124).

The sample-arm lens (144) may comprise an electronically tunable lens (144), for example, a liquid tunable lens, controlled via a tunable lens control signal (180) emanating from a tunable lens driver (178) in the OCT scan device controller (170).

The moveable mirror (148) may also be controlled via a MEMS control signal (176) emanating from a MEMS driver (174) in the OCT scan controller (170).

The OCT scan device controller (170) further includes an OCT scan device central processor (172), an OCT scan device wireless transceiver (186) connected to a corresponding OCT scan device antenna (188) that provides communication with the UI controller (300) as depicted in FIG. 1. Additionally, in an alternative embodiment, the OCT scan device wireless transceiver (186) and corresponding OCT scan device antenna (188) may be replaced with a direct wired communication line with the OCT portable base (200) and/or the UI controller (300).

The OCT scan device (100) further includes an OCT scan device power supply (190) that may comprise a portable battery power source housed within the OCT scan device (100). Alternative embodiments may provide power to the OCT scan device power supply (190) from an independent source such as a main supplied power source outside of the OCT scan device (100), or the OCT portable base power supply (414) as illustrated in FIG. 1.

FIG. 3 illustrates a schematic diagram of a second representative embodiment of the OCT scan device (100) illustrated in FIG. 2 including a fundus imaging system. Reference numbers identical to the first representative embodiment of FIG. 2 are maintained in this description.

Note all bolded lines having a single arrow denote an optical engine uni-directional optical path (10), whereas all bolded lines having arrows on disparate ends denote an optical engine bi-directional optical path (20). Additionally, all broken lines having a single arrow denote a fundus imaging uni-directional optical path (30), whereas all broken lines having arrows on disparate ends denote a fundus imagine bi-directional optical path (40), (see FIG. 2, Legend). In one embodiment, the fundus imaging uni-directional optical path (30) and bi-directional optical path (40) may comprise a near infrared (NIR) wavelength optical signal.

FIG. 3 illustrates the OCT scan device of FIG. 2 with a fundus imaging system (150) in communication with optical light output from the sample-arm (140). This second imaging modality allows a user to directly view the target sample via a digital camera or fundus camera to display and record images of the sample simultaneous with the OCT scan being generated simultaneously by the OCT imaging system.

The fundus imaging system (150) communicates with the UI controller device (300) used for instrument control and image display. The integrated components allow means for controlling the location of the OCT scan. The image recorded by the fundus camera may be displayed on the screen of the UI controller (300), where the user can direct the location of the OCT scan on the target sample by simply tapping, zooming or panning to the desired location on the displayed fundus image.

For example, the optical light reflected off the moveable mirror (148) passes through a fundus ring light (152) which is reflected off a beam splitter (154) to pass through the focusing lens group (160) and the ocular lens (162) to strike the target sample (166) similarly described in FIG. 2. The beam splitter (154) may comprise a polarizing beam splitter, or a wavelength division scheme using a dichroic mirror element.

However, the fundus ring light (152) also transmits optical emissions off the beam splitter (154), (and substantially coincident with the optical light output), to pass through the focusing lens group (160) and the ocular lens (162) to strike the target sample (166). However, the fundus imaging system (150) emissions reflected off the target sample (166) pass through the beam splitter (154), through a fundus imaging system lens (156) and onto a fundus CMOS imaging sensor (158). The fundus imaging system lens (156) may also comprise a tunable lens (156), for example, a liquid tunable lens that is controlled by the tunable lens drive (178) via tunable lens control signals (180), similar to reference-arm tunable lens (134) and sample-arm tunable lens (144).

The liquid tunable lenses identified above as the reference-arm lens (134), sample-arm lens (144) and the fundus imaging system lens (156) may consist, for example, of a focus variable lens that uses a liquid polymer lens, the shape of which is controlled by the application of an electric current to quickly change or tune the particular focal length to a desired value without physical movement of the lens along its focal length axis.

Figure 4:
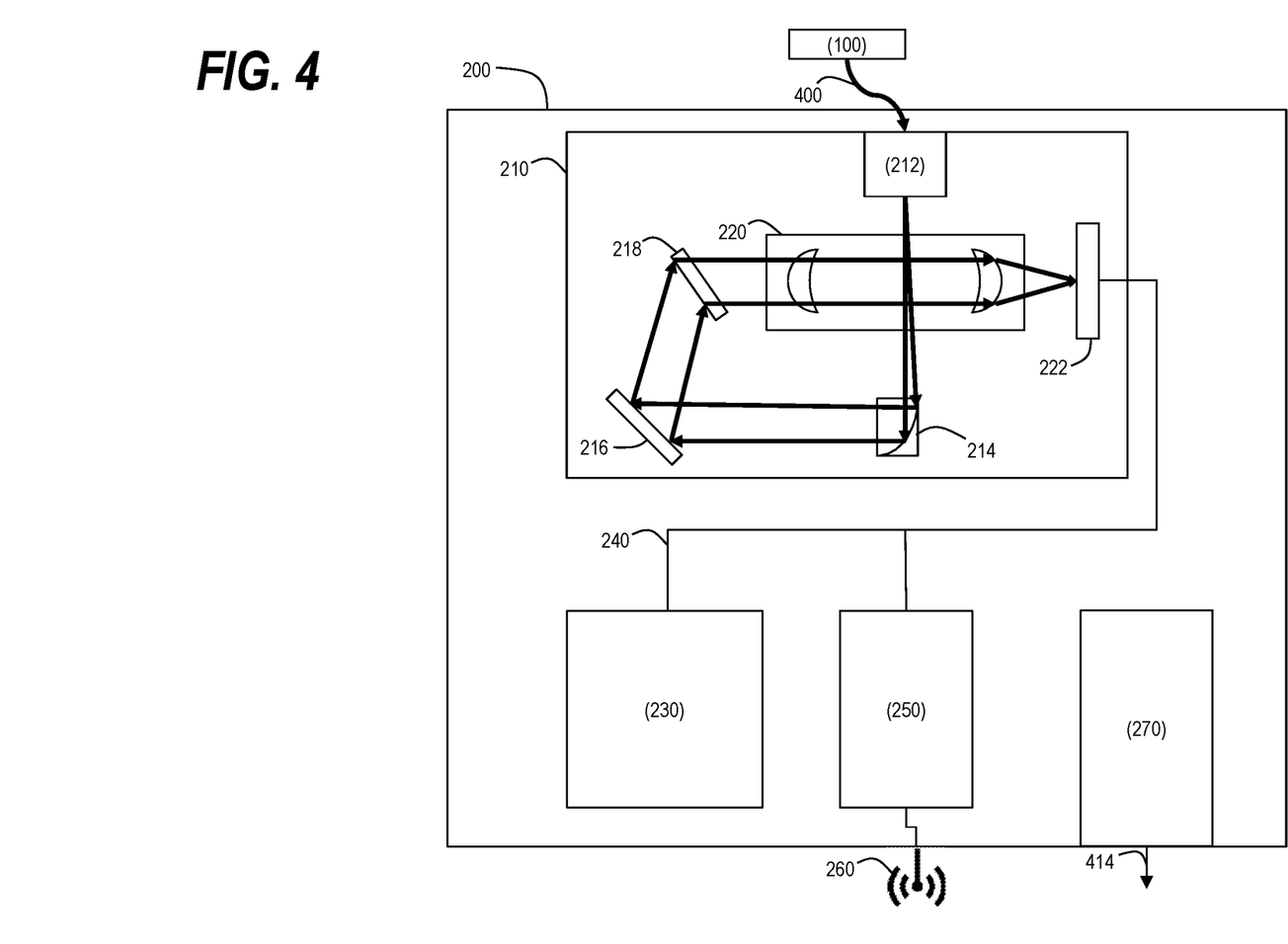
FIG. 4 illustrates a schematic diagram of a portable base that receives interferometer data from the OCT scan device for sensing and conversion to interferometer image data.

FIG. 4 illustrates a schematic diagram of the portable base (200) that receives the interferometer optical output signal (400) from the OCT scan device (100) for sensing and conversion to interferometer image data for display at tomogram images on the display of the UI controller (300).

The interferometer optical output signal (400) from the OCT scan device (100) is received at a spectrometer (210) via a Fiber Coupler/Angled Physical Connection (FC/APC) fiber input (212). The diverging optical signal from FC/APC fiber input (212) is then reflected off an off-axis parabolic mirror (214) which collimates the light and directs the collimated light to be reflected off an OCT portable base folder mirror (216) into a transmission/diffraction grating (218). The light leaving the transmission/diffraction grating (218) is still collimate but at different wavelengths at different angles. The diffracted optical light then passes through a focusing lens group (220) that focuses each wavelength to a particular point onto a tall-pixel CMOS line scan sensor (222) to generate tomographic image data.

The tall-pixel CMOS line scan sensor (222) is in communication with a processor (230), (such as a system-on-module (SOM)), via an OCT portable base communication bus (240) that is also connected to an OCT portable base wireless transceiver (250). The OCT portable base wireless transceiver (250) connected to the OCT portable base antenna (260) receives and transmits control signals (404), and transmits optical coherence tomographic data (408) to the UI controller (300). In an alternative embodiment, OCT portable base wireless transceiver (250) connected to the OCT portable base antenna (260) may be replaced with a hard-wired communication line to communicate with the OCT scan device (100) and/or the UI controller (300).

An OCT portable base power supply (270) provides power to the components of the OCT portable base (200) either via portable battery power supply, or mains power supply. In an alternative embodiment, the OCT portable base power supply (270) may provide power to the OCT scan device (100) via the OCT portable base power supply (414) as illustrated in FIG. 1, and/or may provide power to the UI controller (300).

The spectrometer (210) receives the optical signal from the OCT scan device (100) housing via an optical fiber (400), collimates the output of the optical fiber and directs it to a diffraction grating (218). The diffraction grating (218) may be selected to be polarization insensitive to avoid any effects of signal degradation due to the polarization of the optical field. Light diffracted by the diffraction grating (218) is then refocused (via 220) onto a multi-element sensor (222). The output of the optical fiber may be collimated by an off axis parabolic mirror (214) or a combination of a lens and flat mirror, (not shown). One or more lenses (220) or another parabolic mirror, (not shown), may be used to direct diffracted light to the sensor (222). The sensor (222) may include tall pixels, instead of the usual square pixels, to improve the ease of alignment. The spectrometer (210) body may be fabricated using 3D printing techniques or traditional manufacture.

Another significant advance is the incorporation of processor (230) into the OCT portable base (200). This approach may use a miniaturized PC such as the NUC from Intel™ where all processing components are included in a small form factor or a board level processor such as the system-on-module (SOM) available from multiple manufacturers (Qualcomm™, TI™; AMD™ or Snapdragon™ processors).

The incorporated processor (230) sends electronic control system instructions to the spectrometer (210) and the OCT scan device (100), enabling control of scans, focusing via the tunable lenses (134, 144 and 156), and control of the light source (110). Some embodiments may include electronic control signals for a motorized focus controller (136) of the reference-arm (130) or beam splitter (154). The processor (230) will also receive detected signals from the spectrometer (210) and process the interferometric data to generate tomographic images.

Figure 5:
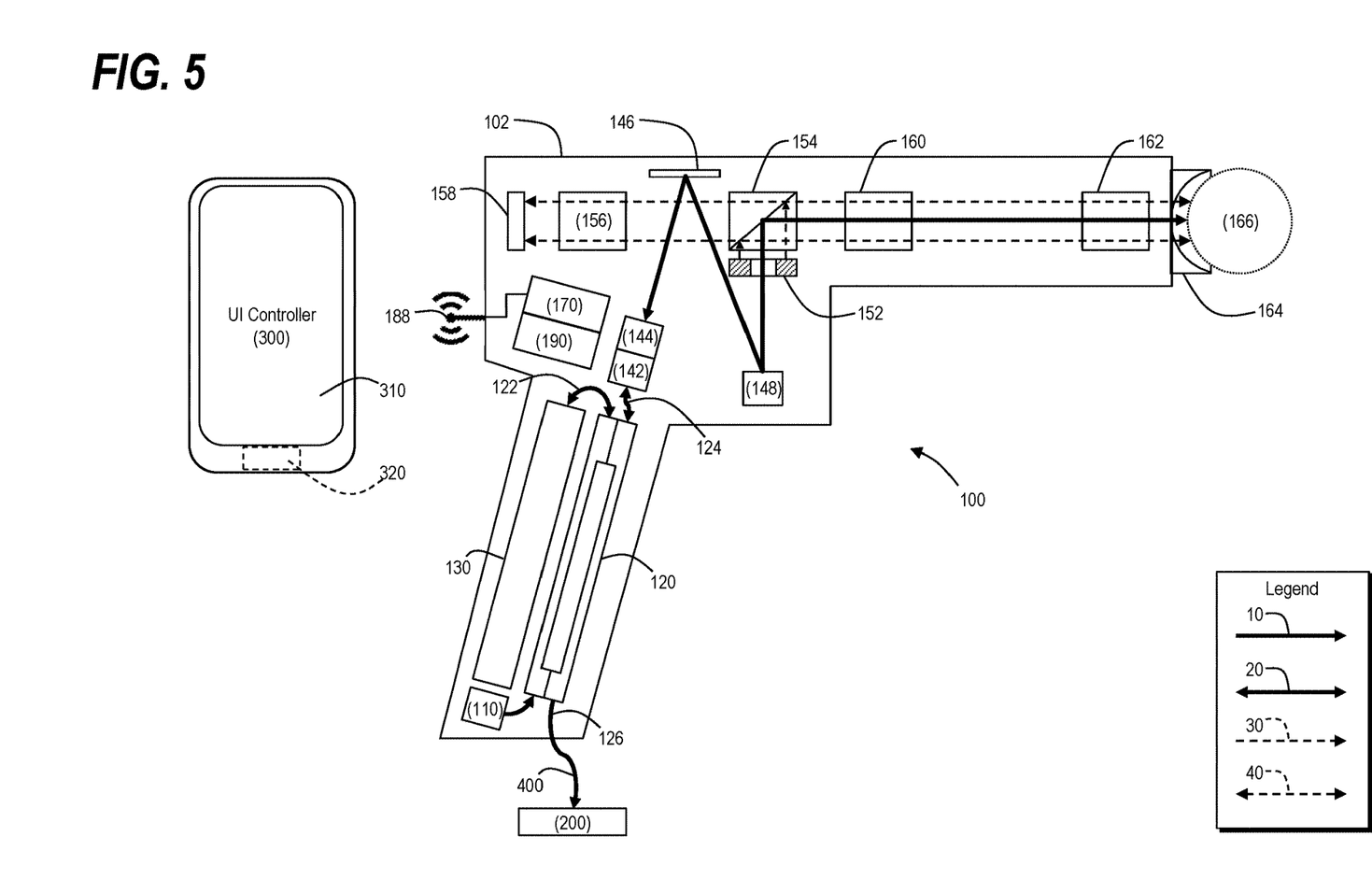
FIG. 5 illustrates a schematic assembly diagram of the second representative embodiment of the OCT scan device of FIG. 2 in communication with the OCT portable base and UI device.

FIG. 5 illustrates a schematic assembly diagram of the second representative embodiment of the OCT scan device (100) of FIG. 2 in communication with the OCT portable base and UI device. Reference numbers identical to the second representative embodiment of FIG. 3 are maintained in this description.

Note all bolded lines having a single arrow denote an optical engine uni-directional optical path (10), whereas all bolded lines having arrows on disparate ends denote an optical engine bi-directional optical path (20). Additionally, all broken lines having a single arrow denote a fundus imaging uni-directional optical path (30), whereas all broken lines having arrows on disparate ends denote a fundus imagine bi-directional optical path (40), (see FIG. 5, Legend).

The OCT scan device (100) has an OCT scan device housing (102) that encloses the illustrated components of FIG. 3. Further illustrated in FIG. 5 is the interferometer (120) and reference-arm (130) being disposed in a substantially parallel configuration in the OCT scan device housing (102). Further illustrated is the sample-arm fold mirror (146) being disposed such that the optical signal from the sample-arm lens (144) passes through a path of the fundus imaging system (150) reflected emissions after they have passed through the beam splitter (154) and is further reflected onto the moveable mirror (148).

In operation, the OCT scan device (100) employs the fundus imaging system (150) as shown in FIG. 3 to generate fundus image data (406) from the fundus CMOS imaging sensor (158). The fundus image data (406) is transmitted via the OCT assembly antenna (188) in communication with the OCT assembly wireless transceiver (186) on the OCT scan device controller (170). The UI controller (300) receives the fundus image data (406) and displays it on the touch input display screen (310). While viewing the fundus image data (406) as a graphical image on the touch input display screen (310), a user may interact with the displayed fundus image to zoom in, zoom out, or pan within the image to select a particular portion of the displayed fundus image and thereby send corresponding control signals (402) to the OCT scan device (100) to activate the MEMs mirror (148) to scan a corresponding portion of the target sample (166).

Thereafter, the reflected optical light from the target sample passes through the interferometer (120) and out of the OCT scan device (100) via the interferometer optical output signal (400) into the spectrometer (210) of the OCT portable base (200) for generation of an optical coherence tomographic image (408). This tomographic image (408) may be sent by the OCT portable base wireless transceiver (250) via the OCT portable base antenna (260) back to the UI controller (300) for display on the touch input display screen (310).

It is noted that by including the majority of components in the portable OCT scan device housing (102), there would be no manipulation of fiber optic components which is known to influence the fidelity of OCT systems. Thus, the embodiments presented herein provide a significant departure from previous OCT systems in that no optical signal is sent to a unit from an independent optical engine. Instead, a substantial portion of the optical engine is included in the OCT scan device (100) itself.

The UI controller (300) may include a smartphone or tablet and receive input from the user comprising parameters for the OCT scan which will be transmitted to the OCT scan device (100) unit via wireless electronic signals (402). The UI controller (300) may alternatively include a display device in combination with user input devices such as a keyboard, mouse and/or touchpad that are either hardwired to or wirelessly communicate with the OCT portable base (200). The UI controller (300) may additionally be hardwired to the OCT portable base (200) for displaying images and receiving user input to control the OCT system (1) via the OCT portable base (200).

In summary, data will be acquired by a user by manually positioning the OCT scan device (100) near the target sample (166) to generate optical signals. These optical signals will be received from the OCT scan device (100) by the OCT portable base (200). The spectrometer (210) within the OCT portable base (200) will convert the optical signals into electronic signals which are received by the processor (230). The processor (230) will use the onboard computer to render tomographic images based on the OCT scans. The rendered images will be transmitted to the user via wireless/Bluetooth link (408) to the UI controller (300) for display.

In some embodiments the processor (230) will also allow automated segmentation and/or analysis of the OCT images. The results of the segmentation and analysis will likewise be transmitted to the UI controller (300)/smartphone for display to the user.

The foregoing presented embodiments are illustrative and are not to be construed as limiting thereof. Although a few exemplary embodiments have been described, those skilled in the art will readily appreciate that many modifications are possible in the exemplary embodiments without materially departing from the novel teachings and its advantages. Accordingly, all such modifications are intended to be included within the scope of the provided embodiments as defined in the claims. In the claims, means-plus function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. An optical coherence tomography (OCT) scan device comprising:
   an OCT scan device housing;
   an interferometer disposed within the OCT scan device housing, the interferometer including
      a light source,
      a fiber optic coupler including an interferometer output,
      a reference-arm, and
      a sample-arm;
   a power source configured to provide power to the light source and the remaining components of the OCT scan device; and
   a controller disposed within the OCT scan device housing and configured to at least one of
      adjust lens focusing parameters in at least one of the reference-arm and the sample-arm, and
      control a scanning function of an optical beam emitting from the sample-arm;
   wherein the OCT scan device being configured to transmit and receive control instructions and transmit fundus image data;
   wherein the reference-arm further comprises:
      a reference-arm collimation lens;
      a reference-arm lens; and
      a reference-arm mirror,
      wherein the reference-arm lens is at least one of controlled by
         a focus controller to adjust a course and fine focus of the reference-arm lens, or
         the controller to electronically control the reference-arm lens, where the reference-arm lens is tunable.

2. The OCT scan device according to claim 1, wherein the fiber optic coupler comprises a fused fiber optic coupler.

3. The OCT scan device according to claim 1, wherein the sample-arm further comprises:
   a sample-arm collimation lens;
   a sample-arm lens that is tunable;
   a sample-arm fold mirror; and
   a moveable mirror.

4. The OCT scan device according to claim 3, further comprising:
   a fundus imaging system disposed within the OCT scan device housing, the fundus imaging system including
      an annular light source,
      a beam splitter,
      a fundus imaging system lens that is tunable, and
      a fundus CMOS imaging sensor,
   wherein the fundus imaging system
      senses optical energy emitted from the annular light source being reflected off a target sample and sensed at the fundus CMOS imaging sensor, and
      generates fundus images from the sensed optical energy.

5. The OCT scan device according to claim 4, wherein the optical beam emitting from the sample-arm being reflected off the moveable mirror passes through a central region of the annular light source and reflects off a reflective surface of the beam splitter.

6. The OCT scan device according to claim 4, wherein a beam emitted from the annular light source and reflected off a reflective surface of the beam splitter travels along a substantially similar path toward a target sample as a path of the optical beam reflected off the reflective surface of the beam splitter.

7. An optical coherence tomography (OCT) system comprising:
   an OCT scan device comprising:
      an OCT scan device housing;
      an interferometer disposed within the OCT scan device housing, the interferometer including a light source,
a beam splitter including an interferometer output,
a reference-arm, and
a sample-arm;
an OCT scan device power source configured to provide power to the light source and the remaining components of the OCT scan device; and
a controller disposed within the OCT scan device housing and configured to at least one of
adjust lens focusing parameters in at least one of the reference-arm and the sample-arm, and
control a scanning function of an optical beam emitting from the sample-arm;
wherein the OCT scan device being configured to transmit and receive control instructions and transmit fundus image data;
an OCT portable base comprising:
a spectrometer including a fiber input in direct communication with the interferometer output of the OCT scan device;
a processor; and
an OCT portable base power supply configured to provide power to the spectrometer and the remaining components of the OCT portable base,
wherein the OCT portable base communicates with the OCT scan device;
wherein the reference-arm further comprises:
a reference-arm collimation lens;
a reference-arm lens; and a reference-arm mirror,
wherein the reference-arm lens is at least one of
operative to adjusting at least one of a course and fine focus of the reference-arm lens, or
operative to be electronically control the reference-arm lens, where the reference-arm lens is tunable.

8. The OCT system according to claim 7, wherein the spectrometer further comprises:
an off-axis parabolic mirror;
a diffraction grating for receiving and dispersing the optical beam emitted from the interferometer output; and
a tall-pixel CMOS line scan sensor for sensing the dispersed optical beam.

9. The OCT system according to claim 7, wherein the OCT scan device further comprises:
a fundus imaging system disposed within the OCT scan device housing, the fundus imaging system including
an annular light source,
a beam splitter,
a fundus imaging system lens that is tunable, and
a fundus CMOS imaging sensor,
wherein the fundus imaging system
senses optical energy emitted from the annular light source being reflected off a target sample and sensed at the fundus CMOS imaging sensor, and
generates fundus images from the sensed optical energy.

10. The OCT system according to claim 9, wherein the sample-arm further comprises a movable mirror, and
wherein the optical beam emitting from the sample-arm being reflected off the moveable mirror passes through the annular light source and reflects off a reflective surface of the beam splitter.

11. The OCT system according to claim 9, wherein the sensed optical energy emitted from the annular light source and reflected off a reflective surface of the beam splitter travels along a substantially similar path toward a target sample as a path of the optical beam reflected off the reflective surface of the beam splitter.

12. The OCT system according to claim 7, wherein the sample-arm further comprises:
a sample-arm collimation lens;
a sample-arm lens that is tunable;
a sample-arm fold mirror; and
a moveable mirror.

* * * * *